(12) United States Patent
Lee et al.

(10) Patent No.: US 10,093,535 B2
(45) Date of Patent: Oct. 9, 2018

(54) MICROCHANNEL RESONATOR AND METHOD FOR MANUFACTURING SAME

(71) Applicant: INDUSTRY-UNIVERSITY COOPERATION FOUNDATION SOGANG UNIVERSITY, Seoul (KR)

(72) Inventors: Jung Chul Lee, Seoul (KR); Joo Hyun Kim, Incheon (KR)

(73) Assignee: INDUSTRY-UNIVERSITY COOPERATION FOUNDATION SOGANG UNIVERSITY (KR)

( * ) Notice: Subject to any disclaimer, the term of this patent is extended or adjusted under 35 U.S.C. 154(b) by 10 days.

(21) Appl. No.: 15/125,070

(22) PCT Filed: Oct. 13, 2014

(86) PCT No.: PCT/KR2014/009555
§ 371 (c)(1),
(2) Date: Sep. 9, 2016

(87) PCT Pub. No.: WO2015/137584
PCT Pub. Date: Sep. 17, 2015

(65) Prior Publication Data
US 2017/0022052 A1 Jan. 26, 2017

(30) Foreign Application Priority Data

Mar. 10, 2014 (KR) .................. 10-2014-0027977
Jul. 2, 2014 (KR) .................. 10-2014-0082564

(51) Int. Cl.
*H01L 27/00* (2006.01)
*H01L 29/00* (2006.01)
(Continued)

(52) U.S. Cl.
CPC ........ *B81C 1/00071* (2013.01); *B81C 1/0015* (2013.01); *G01N 5/00* (2013.01);
(Continued)

(58) Field of Classification Search
CPC .......... G01N 5/00; G01N 9/00; G01N 29/022; G01N 29/036; H01L 31/0352
See application file for complete search history.

(56) References Cited

U.S. PATENT DOCUMENTS 6,116,756 A * 9/2000 Peeters ............... H01S 5/02252
257/E27.12
7,282,329 B2 10/2007 Manalis et al.
(Continued)

FOREIGN PATENT DOCUMENTS

JP 2001507801 A 6/2001
KR 100425677 B1 4/2004
KR 1020090113643 A 11/2009

*Primary Examiner* — Quovaunda V Jefferson
(74) *Attorney, Agent, or Firm* — Kunzler, PC

(57) ABSTRACT

Provided is a method for manufacturing a microchannel resonator capable of measuring a mass and characteristics of an object using a principle in which a resonance frequency is changed according to a mass of a moving material, the method including: providing a silicon substrate; forming a cavity channel inside the silicon substrate; forming a hollow silicon oxide structure on the inner wall surface of the cavity channel by oxidizing the inner wall surface of the cavity channel; and partially removing the periphery of the hollow silicon oxide structure such that the hollow silicon oxide structure can resonate with respect to the silicon substrate.

14 Claims, 12 Drawing Sheets

(51) Int. Cl.
*B81C 1/00* (2006.01)
*G01N 29/036* (2006.01)
*G01N 5/00* (2006.01)
*G01N 9/00* (2006.01)
*G01N 29/02* (2006.01)
*H01L 31/0352* (2006.01)

(52) U.S. Cl.
CPC ........... *G01N 9/002* (2013.01); *G01N 29/022* (2013.01); *G01N 29/036* (2013.01); *B81B 2201/0271* (2013.01); *B81B 2201/058* (2013.01); *G01N 2291/0256* (2013.01); *H01L 31/0352* (2013.01)

(56) References Cited

U.S. PATENT DOCUMENTS

| | | | | |
|---|---|---|---|---|
| 2002/0113523 A1* | 8/2002 | Endoh | ................... | H03H 9/1021 310/344 |
| 2007/0063648 A1* | 3/2007 | Ogata | ................. | H04M 1/0266 313/512 |
| 2011/0183456 A1* | 7/2011 | Hsieh | ................. | B81C 1/00246 438/53 |
| 2011/0284995 A1* | 11/2011 | Kuypers | ................... | B81B 7/02 257/622 |

* cited by examiner

[Fig. 1]
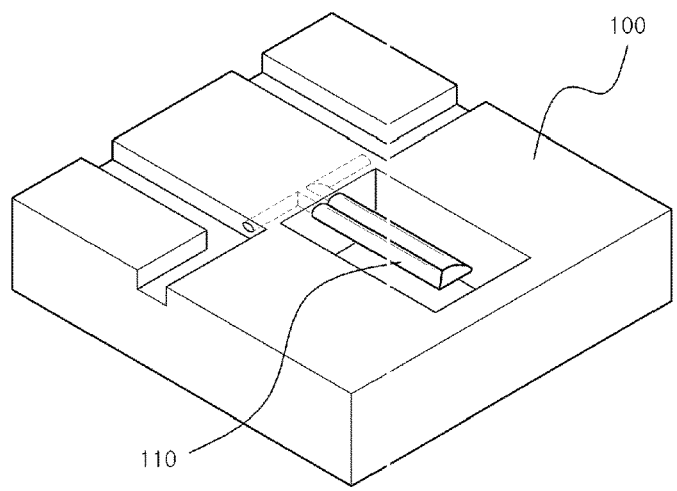
[Fig. 2]
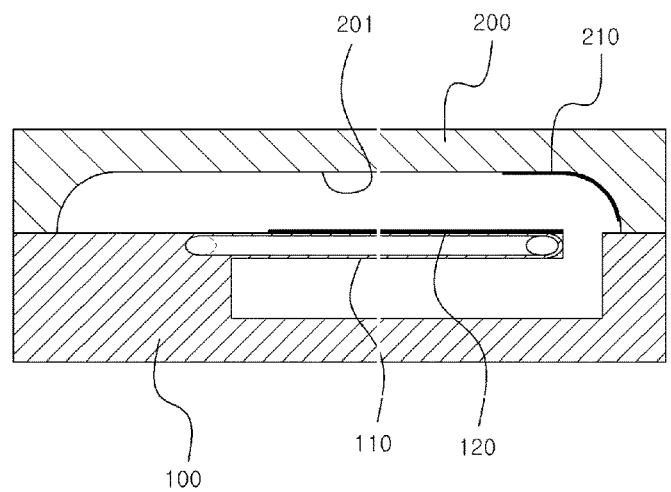
[Fig. 3]
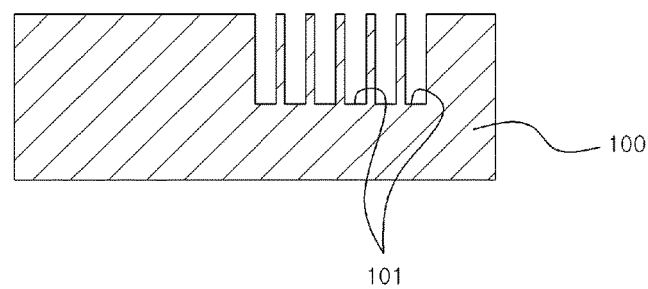

[Fig. 4]
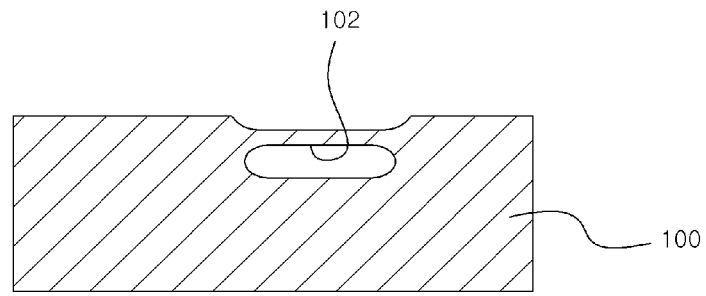
[Fig. 5]
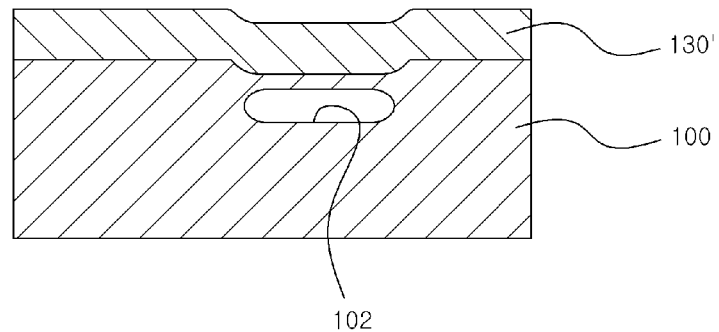
[Fig. 6]
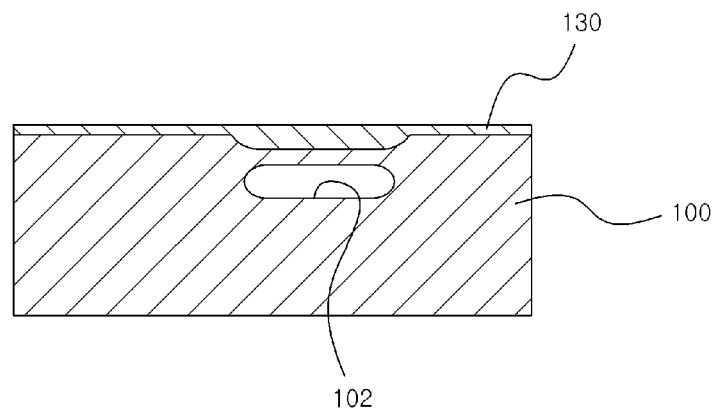

[Fig. 7]
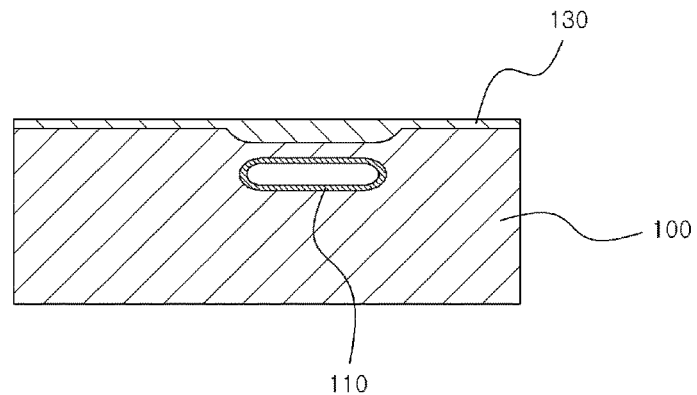
[Fig. 8]
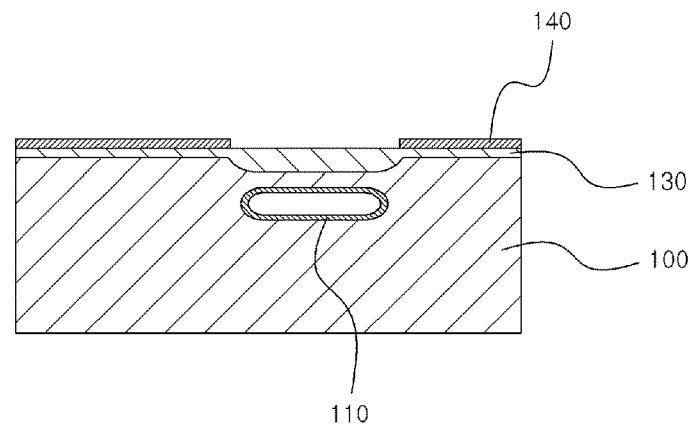
[Fig. 9]
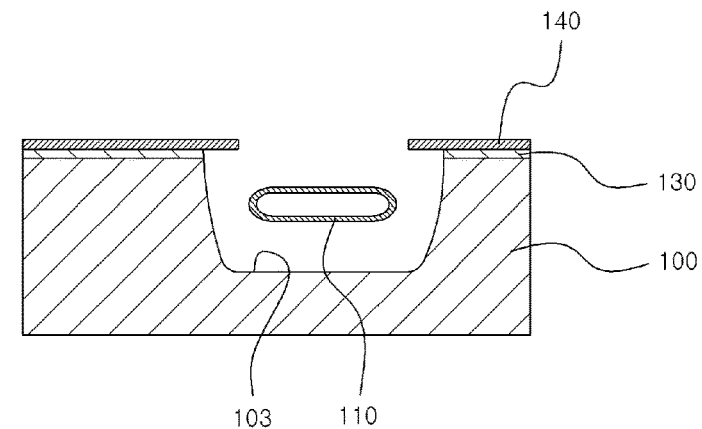

[Fig. 10]
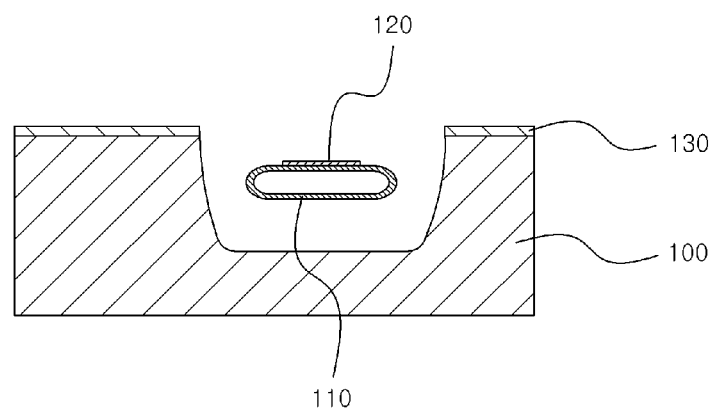
[Fig. 11]
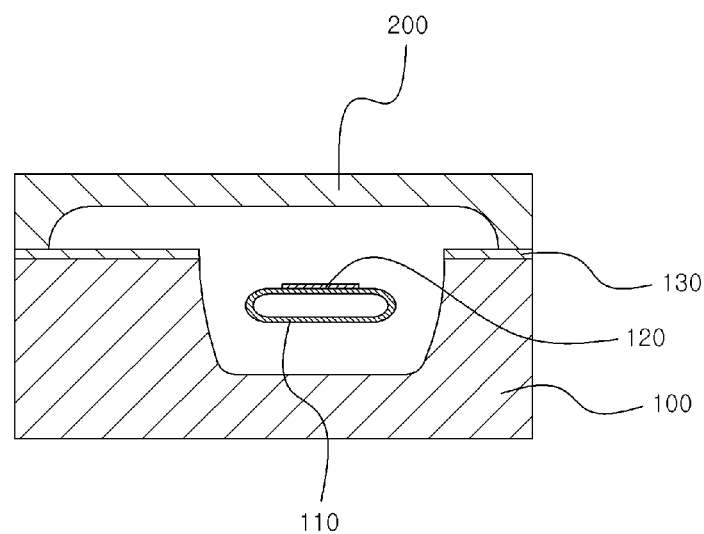

[Fig. 12]
(a)
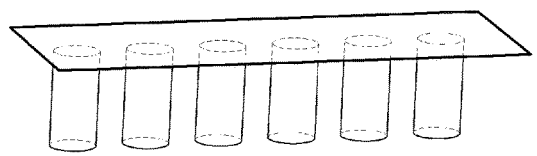
(b)
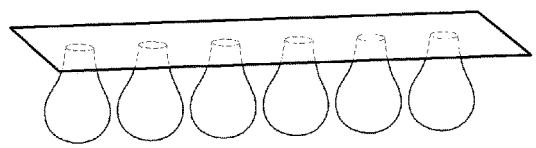
(c)
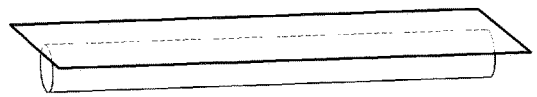
[Fig. 13]
| $S_H$ \ $\Phi_H$ | 1.0 | 1.4 | 1.8 | 2.2 | 2.6 |
|---|---|---|---|---|---|
| 0.4 | | | | | |
| 0.6 | | | | | |
| 0.8 | | | | | |
| 1.0 | | | | | |
| 1.2 | | | | | |

[Fig. 14]
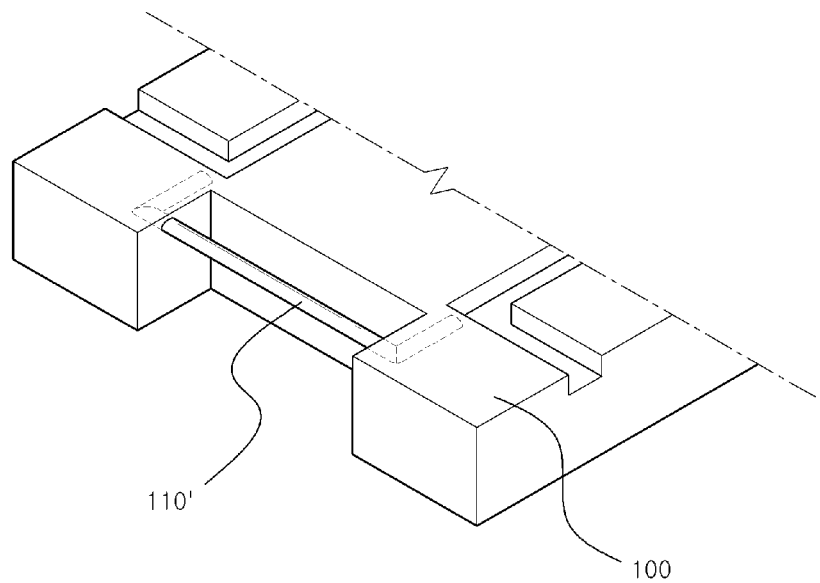
[Fig. 15]
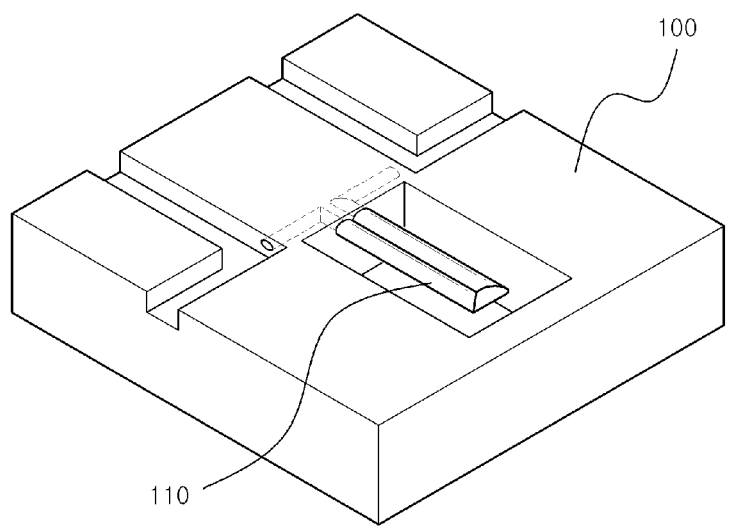

[Fig. 16]
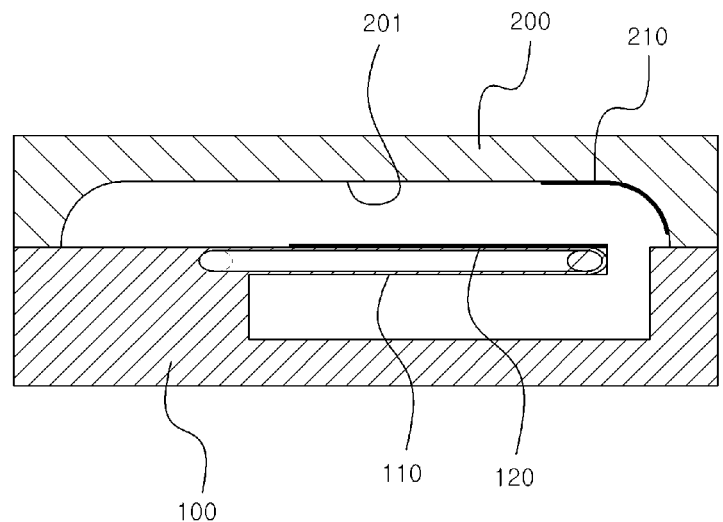
[Fig. 17]
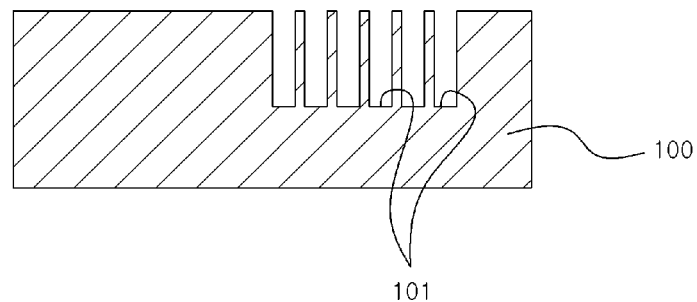
[Fig. 18]
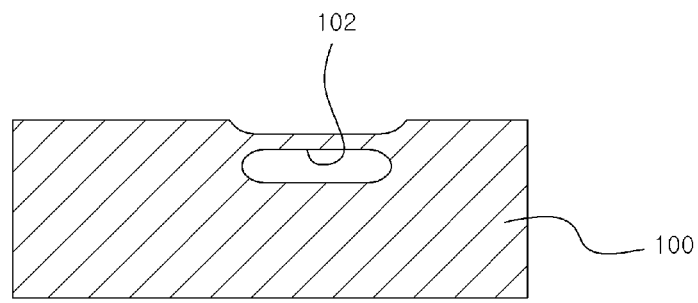

[Fig. 19]
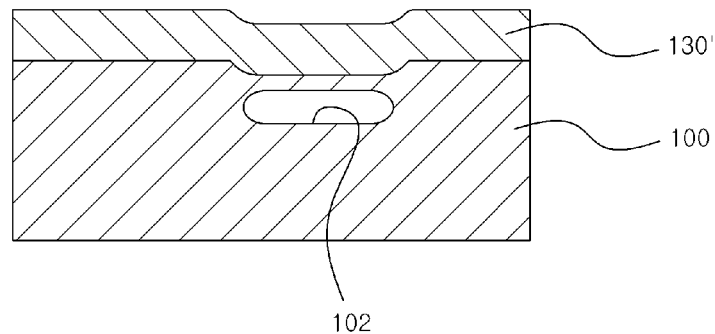
[Fig. 20]
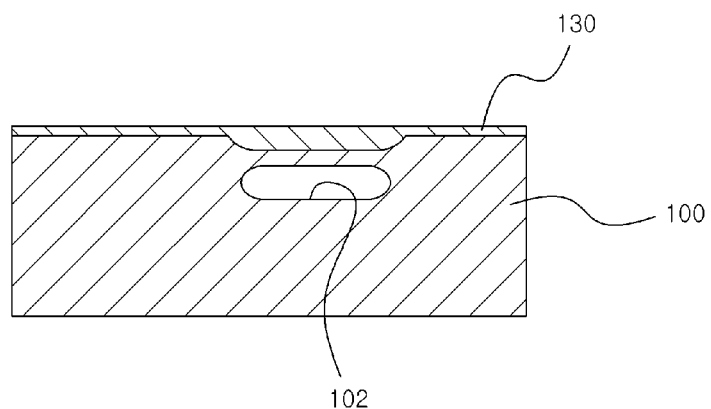
[Fig. 21]
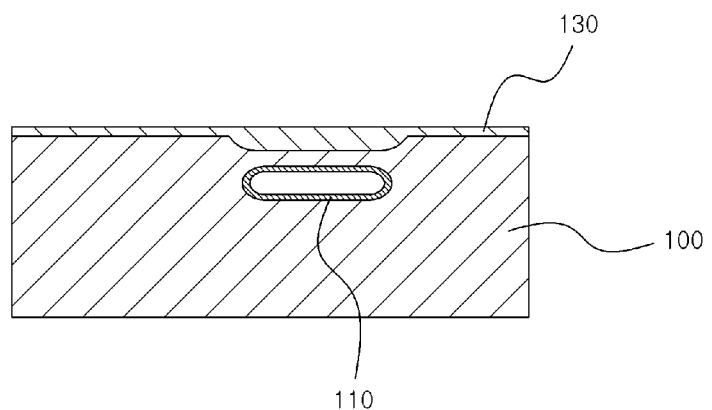

[Fig. 22]
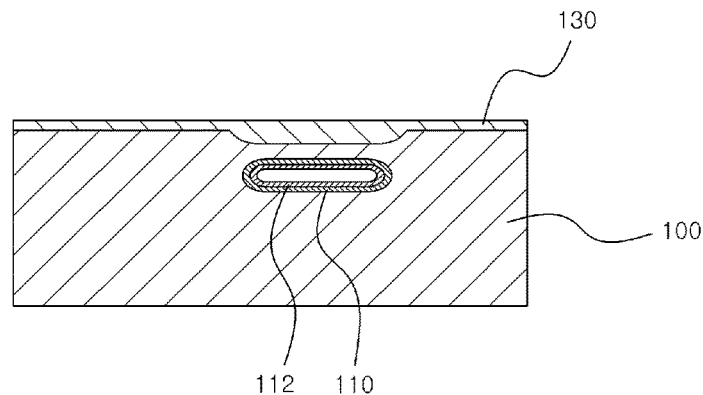
[Fig. 23]
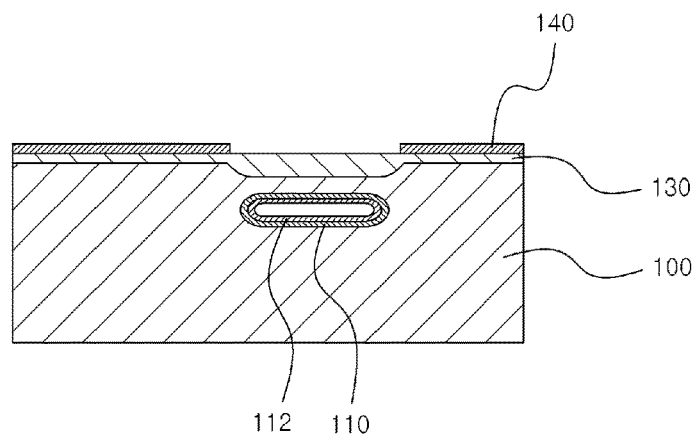
[Fig. 24]
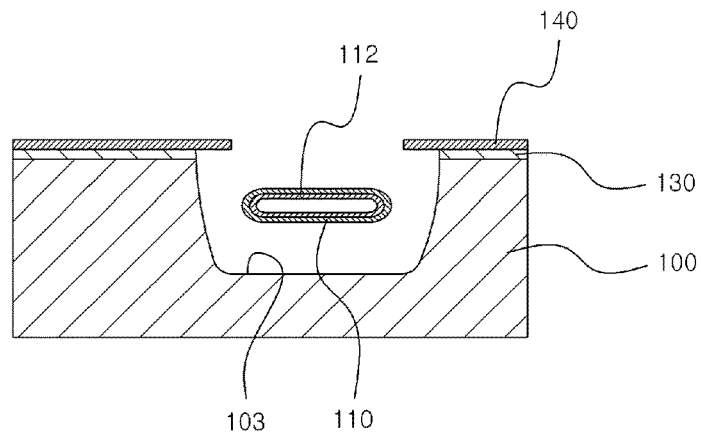

[Fig. 25]
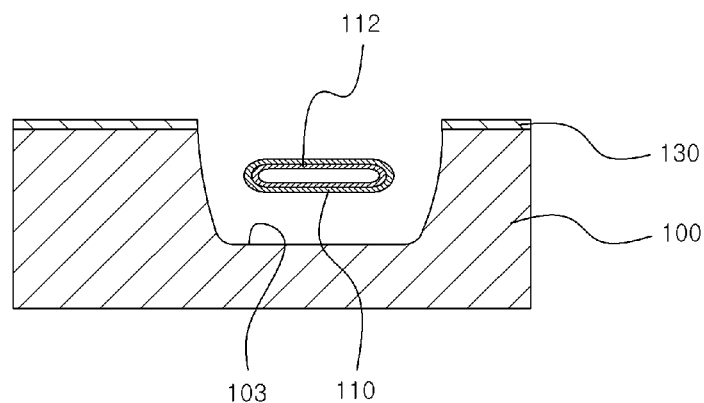
[Fig. 26]
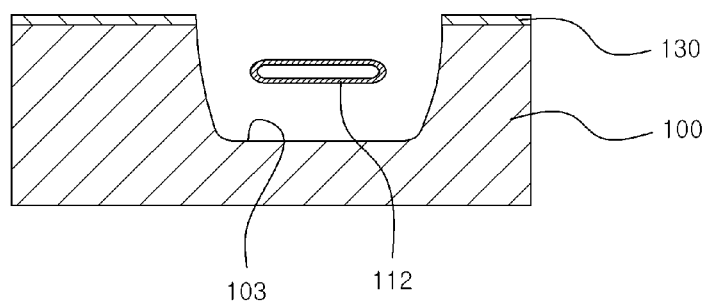

[Fig. 27]
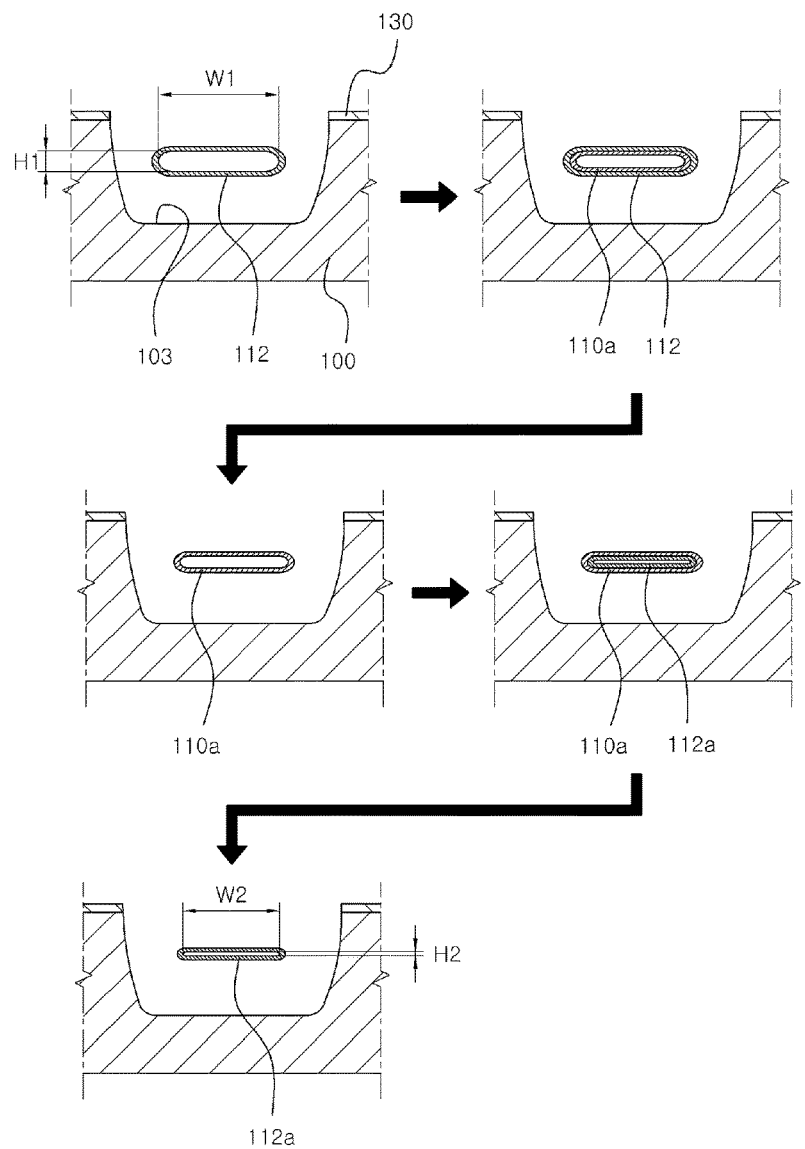
[Fig. 28]
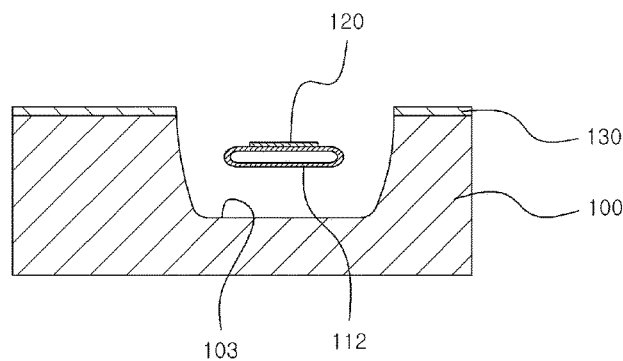

[Fig. 29]
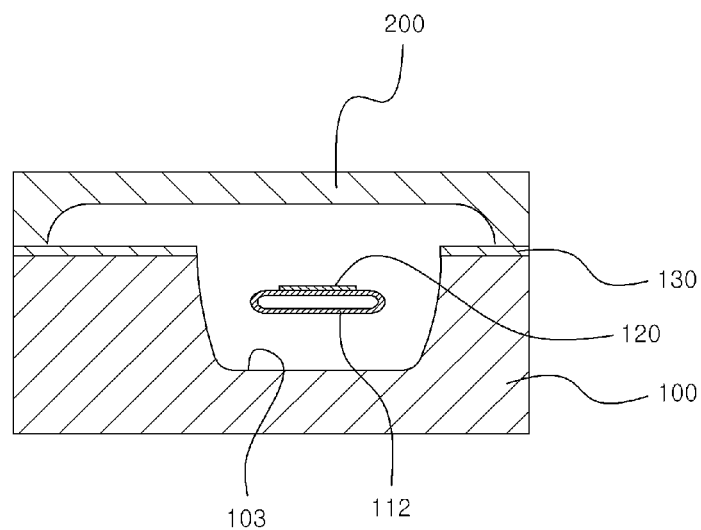

MICROCHANNEL RESONATOR AND METHOD FOR MANUFACTURING SAME

TECHNICAL FIELD

The present invention relates to a microchannel resonator and a method for manufacturing the same, and more particularly, to a microchannel resonator and a method for manufacturing the same capable of measuring the mass and characteristics of an object by using a principle in which a resonance frequency is changed according to the mass of a moving material.

BACKGROUND ART

NanoBioMEMS technologies mean intellectualized and automated micromechanical medical/chemical equipment capable of immediately sensing, measuring, analyzing and diagnosing physical, chemical and biological interactions between biomolecules.

As one of NanoBioMEMS technologies, conventional microchannel resonant balances (microbalances, microcantilevers) capable of measuring weights of single living cells to a femtogram unit have been suggested and conventional microchannel resonant balances are disclosed in U.S. Pat. No. 7,282,329 (Oct. 16, 2007).

A measurement principle of conventional microchannel resonant balances is as follows. A hollow resonator is made and a fluidic liquid molecular sample is injected thereto. The resonator is surrounded with a vacuum, while the liquid phase of fluid molecules are disposed in the resonator. In a case where the fluid sample disposed in the resonator includes solid particles, a vibration frequency of the resonator is measured when the solid particles move in the resonator, such that the mass of the particles can be precisely measured.

However, conventional microchannel resonant balances have problems in that they are very difficult to form and are not easy to manufacture because they require a delicate and complicated manufacturing process. In particular, conventional microchannel resonant balances have problems of complicated manufacturing process and increased manufacturing time because sections for microchannels should first be formed on a silicon substrate and complicated patterning and etching processes entailing various steps should then be performed for forming beams of microcantilever structures including the microchannels using the sections.

Accordingly, recently, various researches have been made to simplify the structure and manufacturing process of microchannel resonators, but they are insufficient and there is thus a need for development thereof.

Further, recently, a channel resonator by a nano-scale unit has been required so as to measure various characteristics of the object in much various conditions, but it is difficult to manufacture the resonator by the nano-scale unit by the existing manufacturing process and thus the development thereof has been urgently required.

DISCLOSURE

Technical Problem

Therefore, it is one object of the present invention to provide a microchannel resonator and a method for manufacturing the same, capable of simplifying a structure and a manufacturing process thereof.

In particular, it is another object of the present invention to provide a microchannel resonator and a method for manufacturing the same that can form a cavity channel inside a silicon substrate and form a pipe-shaped hollow silicon oxide structure by oxidizing the inner wall surface of the cavity channel.

In addition, it is another object of the present invention to provide a microchannel resonator and a method for manufacturing the same capable of forming a microchannel structure by forming a cavity channel inside a silicon substrate, forming a hollow silicon oxide structure by oxidizing the inner wall surface of the cavity channel, and then forming a hollow polysilicon structure on the inner wall surface of the hollow silicon oxide structure.

In addition, it is another object of the present invention to provide a microchannel resonator and a method for manufacturing the same capable of manufacturing a channel resonator by a nano-scale unit as well as a micro-scale unit.

In addition, it is another object of the present invention to provide a microchannel resonator and a method for manufacturing the same capable of forming a pipe-shaped microchannel structure in various conditions and shapes.

In addition, it is another object of the present invention to provide a microchannel resonator and a method for manufacturing the same capable of improving structural stability and reliability.

In addition, it is another object of the present invention to provide a microchannel resonator and a method for manufacturing the same capable of reducing manufacturing costs and applicable to various NanoBioMEMS devices and fields.

Technical Solution

In accordance with an aspect of the present invention, the above and other objects can be accomplished by the provision of a method for manufacturing a microchannel resonator capable of measuring a mass and characteristics of an object using a principle in which a resonance frequency is changed according to a mass of a moving material, the method including: providing a silicon substrate; forming a cavity channel inside the silicon substrate; forming a hollow silicon oxide structure on the inner wall surface of the cavity channel by oxidizing the inner wall surface of the cavity channel; and partially removing the periphery of the hollow silicon oxide structure such that the hollow silicon oxide structure can resonate with respect to the silicon substrate.

The cavity channel inside the silicon substrate may be formed by various methods according to requirements and design specifications. For example, the forming of the cavity channel inside the silicon substrate may include forming a plurality of trenches on the silicon substrate, and annealing the silicon substrate to form the cavity channel inside the silicon substrate by using the plurality of trenches, in which during the annealing of the silicon substrate, the adjacent trenches may be connected to each other and cooperatively form the cavity channel.

The trenches for forming the cavity channel may be formed by various methods according to requirements. For example, the forming of the trenches may include patterning a first photoresist pattern on the silicon substrate, first-etching the surface of the silicon substrate by using the first photoresist pattern, and removing the first photoresist pattern, in which the trenches may be formed to have a predetermined depth during the first etching.

The silicon substrate with the trenches may be annealed under predetermined temperature, pressure and time conditions, thereby forming the cavity channel using the trenches inside the silicon substrate. When the silicon substrate with the trenches is annealed, upper end openings of the trenches become slowly narrower and then closed, like approximately water drops, and at the same time, lower ends of the trenches become wider. At this time, the lower ends of adjacent trenches are connected to each other, thereby cooperatively forming the cavity channel inside the silicon substrate by the adjacent trenches.

In addition, after forming the cavity channel inside the silicon substrate, a polysilicon thin film layer (Poly-Si LPCVD) may be formed on an upper surface of the silicon substrate. For example, the polysilicon thin film layer may be provided by depositing a polysilicon layer on the upper surface of the silicon substrate and polishing the upper surface of the silicon substrate such that an upper recess of the polysilicon layer is removed. In some cases, another means instead of the polysilicon thin film layer may be used as an alternative means, or the polysilicon thin film layer may be removed.

The microstructure is a silicon oxide film formed by oxidizing the inner wall surface of the cavity channel formed inside the silicon substrate and may be formed in a hollow pipe shape corresponding to the cavity channel along the inner wall surface of the cavity channel. Unlike the related art, in the present invention, without performing patterning and etching processes in several complicated steps in order to form the hollow silicon oxide structure, simply, the hollow silicon oxide structure may be formed by supplying oxygen along the inner space of the cavity channel and oxidizing the inner wall surface of the cavity channel.

For reference, herein, the case where the hollow silicon oxide structure is partially removed such that the hollow silicon oxide structure can resonate with respect to the silicon substrate can be understood as the case where a resonance space is formed by partially removing the silicon substrate portion corresponding to the periphery of the hollow silicon oxide structure so as to have a structure in which the hollow silicon oxide structure can resonate with respect to the silicon substrate.

The hollow silicon oxide structure may have various structures, as a structure in which the hollow silicon oxide structure can resonate with respect to the silicon substrate, according to requirements and design specifications. For example, by partially removing the periphery of the hollow silicon oxide structure, the hollow silicon oxide structure may be provided in a cantilever structure having a fixed end at one end and a free end at the other end. As another example, by partially removing the periphery of the hollow silicon oxide structure, the hollow silicon oxide structure may be provided in a bridge structure having fixed ends at both ends.

The process of removing the periphery of the hollow silicon oxide structure may be implemented by various methods according to requirements and design specifications. As an example, the partially removing of the periphery of the hollow silicon oxide structure may include patterning a second photoresist pattern on the upper surface of the silicon substrate, partially second-etching the periphery of the hollow silicon oxide structure in the silicon substrate by using the second photoresist pattern, and removing the second photoresist pattern.

In addition, a first electrode layer may be formed on an upper surface of the hollow silicon oxide structure before adhering the glass substrate, and the glass substrate may include a second electrode layer for cooperatively and electrostatically interacting with the first metal layer.

The glass substrate may be provided by various methods according to requirements and design specifications. For example, the glass substrate may be provided by patterning a third photoresist pattern on the surface of the glass substrate, forming a resonance space on the surface of the glass substrate by third-etching the surface of the glass substrate by using the third photoresist pattern, and forming the second electrode layer on the resonance space. In some cases, the hollow silicon oxide structure may be configured to resonate by other mechanical excitation methods.

In accordance with another aspect of the present invention, the above and other objects can be accomplished by the provision of a method for manufacturing a microchannel resonator capable of measuring a mass and characteristics of an object using a principle in which a resonance frequency is changed according to a mass of a moving material, the method including: providing a silicon substrate; forming a cavity channel inside the silicon substrate; forming a hollow silicon oxide structure on the inner wall surface of the cavity channel by oxidizing the inner wall surface of the cavity channel; forming a hollow polysilicon structure on the inner wall surface of the hollow silicon oxide structure, and selectively removing the periphery of the hollow polysilicon structure such that the hollow polysilicon structure can resonate with respect to the silicon substrate, in which a hollow microchannel structure is provided such that the moving material resonates by the remaining hollow polysilicon structure by selectively removing the periphery of the hollow polysilicon structure.

The cavity channel inside the silicon substrate may be formed by various methods according to requirements and design specifications. For example, the forming of the cavity channel inside the silicon substrate may include forming a plurality of trenches on the silicon substrate, and annealing the silicon substrate to form the cavity channel inside the silicon substrate by using the plurality of trenches, in which during the annealing of the silicon substrate, the adjacent trenches may be connected to each other and cooperatively form the cavity channel.

The trenches for forming the cavity channel may be formed by various methods according to requirements. For example, the forming of the trenches may include patterning a first photoresist pattern on the silicon substrate, first-etching the surface of the silicon substrate by using the first photoresist pattern, and removing the first photoresist pattern, in which the trenches may be formed to have a predetermined depth during the first etching.

The silicon substrate with the trenches may be annealed under predetermined temperature, pressure and time conditions, thereby forming the cavity channel using the trenches inside the silicon substrate. When the silicon substrate with the trenches is annealed, upper end openings of the trenches become slowly narrower and then closed, like approximately water drops, and at the same time, lower ends of the trenches become wider. At this time, the lower ends of adjacent trenches are connected to each other, thereby cooperatively forming the cavity channel inside the silicon substrate by the adjacent trenches.

In addition, after forming the cavity channel inside the silicon substrate, a polysilicon thin film layer (Poly-Si LPCVD) may be formed on an upper surface of the silicon substrate. For example, the polysilicon thin film layer may be provided by depositing a polysilicon layer on the upper surface of the silicon substrate and polishing the upper surface of the silicon substrate such that an upper recess of the polysilicon layer is removed. In some cases, another means instead of the polysilicon thin film layer may be used as an alternative means, or the polysilicon thin film layer may be removed.

The microchannel structure may be provided by forming the cavity channel inside the silicon substrate, forming the hollow silicon oxide structure by oxidizing the inner wall surface of the cavity channel, and then forming the hollow polysilicon structure on the inner wall surface of the hollow silicon oxide structure. Unlike the related art, in the present invention, without performing patterning and etching processes in several complicated steps in order to form the microchannel structure, simply, the hollow microchannel structure may be formed by supplying oxygen along the inner space of the cavity channel and oxidizing the inner wall surface of the cavity channel and then forming the hollow polysilicon structure on the inner wall surface of the hollow silicon oxide structure.

For reference, the case where the hollow polysilicon structure is selectively removed such that the hollow polysilicon structure can resonate with respect to the silicon substrate can be understood as the case where a resonance space is formed by partially removing the silicon substrate portion corresponding to the periphery of the hollow polysilicon structure and the hollow silicon oxide structure so as to have a structure in which the hollow polysilicon structure can resonate with respect to the silicon substrate.

As a structure in which the microchannel structure configured by the hollow polysilicon structure can resonate with respect to the silicon substrate, various structures may be applied according to requirements and design specifications. For example, by selectively removing the periphery of the hollow polysilicon structure, the microchannel structure configured by the hollow polysilicon structure may be provided in a cantilever structure having a fixed end at one end and a free end at the other end. As another example, selectively removing the periphery of the hollow polysilicon structure, the microchannel structure configured by the hollow polysilicon structure may be provided in a bridge structure having fixed ends at both ends.

The process of removing the silicon substrate portion corresponding to the periphery of the hollow polysilicon structure may be implemented by various methods according to requirements and design specifications. As an example, in the selectively removing of the periphery of the hollow polysilicon structure such that the hollow polysilicon structure resonates with respect to the silicon substrate, the silicon substrate and the hollow polysilicon structure may be removed by a single removing process or a plurality of removing processes.

The method for manufacturing a microchannel resonator may further include forming a second hollow silicon oxide structure on the inner wall surface of the hollow polysilicon structure by oxidizing the inner wall surface of the hollow polysilicon structure, forming a second hollow polysilicon structure inside the second hollow silicon oxide structure, and removing the second hollow silicon oxide structure, in which the microchannel structure may be defined by the second hollow polysilicon structure and a height and a width of the microchannel structure may be reduced by using the second hollow silicon oxide structure and the second hollow polysilicon structure.

In addition, a first electrode layer may be formed on an upper surface of the microchannel structure before adhering the glass substrate, and the glass substrate may include a second electrode layer for cooperatively and electrostatically interacting with the first metal layer.

The glass substrate may be provided by various methods according to requirements and design specifications. For example, the glass substrate may be provided by patterning a third photoresist pattern on the surface of the glass substrate, forming a resonance space on the surface of the glass substrate by third-etching the surface of the glass substrate by using the third photoresist pattern, and forming the second electrode layer on the resonance space. In some cases, the microchannel structure may be configured to resonate by other mechanical excitation methods.

Advantageous Effects

According to the microchannel resonator and the manufacturing method the same according to the present invention, structure and manufacturing process can be simplified.

In particular, according to the present invention, a pipe-shaped hollow silicon oxide structure can be formed by forming a cavity channel inside the silicon substrate and simply oxidizing the inner wall surface of the cavity channel, thereby omitting complicated patterning and etching processes in many steps, involved in conventional methods and forming the hollow silicon oxide structure by a relatively simple process.

Furthermore, according to the present invention, the cavity channel inside the silicon substrate can be formed by a relatively simple process such as annealing the silicon substrate after forming a plurality of trenches on the silicon substrate, thereby further simplifying the structure and the manufacturing process.

In addition, according to the present invention, cavity channels having various shapes and structures can be formed according to requirements and design specifications and the hollow silicon oxide structure can be formed based on the cavity channel, thereby forming the hollow silicon oxide structure in much various conditions and shapes without limitation of the structure and the manufacturing process. Further, according to the present invention, the microchannel structure can be formed by forming the cavity channel inside the silicon substrate, forming the hollow silicon oxide structure by oxidizing the inner wall surface of the cavity channel, and then forming the hollow silicon oxide structure on the inner wall surface of the hollow silicon oxide structure, thereby omitting complicated patterning and etching processes in many steps like the related art and forming a microchannel structure by a relatively simple process.

Further, according to the present invention, the height and width of the microchannel structure can be reduced through the processes of forming and removing the second hollow silicon oxide structure and the second hollow polysilicon structure inside the microchannel structure. Particularly, according to the present invention, the processes of forming and removing the second hollow silicon oxide structure and the second hollow polysilicon structure are repetitively performed, thereby forming a channel structure having very small width and height. Accordingly, according to the present invention, a channel resonator of a nano-scale unit as well as a micro-scale unit can be manufactured.

Meanwhile, the channel resonator of the nano-scale unit can be formed by forming trenches for forming the cavity channel with a very fine size (a nano scale), but in order to form the trenches with the very fine size, there is a problem in that complicated manufacturing processes need to be performed by using expensive specific equipment. However, according to the present invention, without forming the trenches having the very fine sizes, simply, the processes of forming and removing the second hollow silicon oxide structure and the second hollow polysilicon structure inside the microchannel structure are repetitively performed to manufacture a channel resonator of a nano-scale unit, thereby further simplifying the manufacturing process and reducing the manufacturing costs.

In addition, according to the present invention, cavity channels having various shapes and structures can be formed according to requirements and design specifications and the microchannel structure can be formed based on the cavity channel, thereby forming the microchannel structure in much various conditions and shapes without limitation of the structure and the manufacturing process.

In addition, according to the present invention, structural stability and reliability can be improved.

In addition, according to the present invention, various chips can be designed and conditions and shapes of microchannels can be varied, thereby being freely applicable to various research and industrial fields.

DESCRIPTION OF DRAWINGS

The above and other objects, features and other advantages of the present invention will be more clearly understood from the following detailed description taken in conjunction with the accompanying drawings, in which:

FIGS. 1 and 2 are diagrams for describing a microchannel resonator according to the present invention;

FIGS. 2 to 11 are diagrams for describing a method for manufacturing a microchannel resonator according to the present invention;

FIGS. 12 and 13 are diagram for describing a principle and an example in which a cavity channel is formed by annealing, in the method for manufacturing a microchannel resonator according to the present invention;

FIG. 14 is a diagram for describing a microchannel resonator according to another embodiment of the present invention;

FIGS. 15 and 16 are diagrams for describing a microchannel resonator according to the present invention; and FIGS. 17 to 29 are diagrams for describing a method for manufacturing a microchannel resonator according to the present invention.

BEST MODE

Hereinafter, preferred embodiments of the present invention will be described in detail with reference to the annexed drawings, but should be not construed as limiting or restricting the present invention. For reference, the same reference numbers will be used throughout the drawings to refer to substantially same elements. Such a condition, contents described in other drawings may be cited for a more thorough description and contents that may be determined obvious to those skilled in the art or repeated contents may be omitted.

FIGS. 1 and 2 are diagrams for describing a microchannel resonator according to the present invention, FIGS. 2 to 11 are diagrams for describing a method for manufacturing a microchannel resonator according to the present invention, and FIGS. 12 and 13 are diagram for describing a principle and an example in which a cavity channel is formed by annealing, in the method for manufacturing a microchannel resonator according to the present invention. Further, FIG. 14 is a diagram for describing a microchannel resonator according to another embodiment of the present invention.

For reference, the microchannel resonator according to the present invention may be used to measure mass and characteristics of objects. In some cases, the microchannel resonator according to the present invention may be used to sense, measure, analyze and diagnose of physical, chemical and biological interactions of objects and the present invention is not limited to the usage thereof.

Referring to FIGS. 1 and 2, the microchannel resonator according to the present invention includes a silicon substrate 100 and a glass substrate 200.

A hollow microchannel structure 110 is provided on the silicon substrate 100 such that it can resonate, and the hollow microchannel structure 110 can resonate by electrostatic interaction between a first electrode layer 120 formed on the upper surface of the hollow microchannel structure 110 and a second electrode layer 210 provided on the glass substrate 200.

The hollow microchannel structure may form a cavity channel 102 inside the silicon substrate 100 and may be simply formed in a hollow pipe shape by oxidizing the inner wall surface of the cavity channel 102.

For reference, the hollow microchannel structure 110 may be provided in a cantilever structure which has a fixed end at one end and a free end at the other end. In some cases, the hollow microchannel structure 110 may be provided in a bridge structure which has fixed ends at both ends.

Hereinafter, a method for manufacturing a microchannel resonator according to the present invention will be described.

The method for manufacturing the microchannel resonator according to the present invention includes providing a silicon substrate 100, forming a cavity channel 102 inside the silicon substrate 100, forming a hollow silicon oxide structure 110 on the inner wall surface of the cavity channel 102 by oxidizing the inner wall surface of the cavity channel 102, partially removing the periphery of the hollow silicon oxide structure 110 such that the hollow silicon oxide structure 110 can resonate with respect to the silicon substrate 100, and adhering a glass substrate 200 on the upper surface of the silicon substrate 100.

First, the silicon substrate 100 is provided and the cavity channel 102 is formed inside the silicon substrate 100.

The cavity channel 102 inside the silicon substrate 100 may be formed by various methods according to requirements and design specifications. For example, the forming of the cavity channel 102 inside the silicon substrate 100 may include forming a plurality of trenches 101 on the silicon substrate 100, and annealing the silicon substrate 100 using the plurality of trenches 101 so as to form the cavity channel 102 inside the silicon substrate 100, and during annealing of the silicon substrate 100, the adjacent trenches 102 are connected to each other to cooperatively form the cavity channel 102.

Referring to FIG. 3, the plurality of trenches 101 may be formed on the silicon substrate 100 at a predetermined array. The trenches 101 may be formed by various methods according to requirements. For example, the forming of the trenches 101 may include patterning a first photoresist pattern on the silicon substrate 100, first-etching the surface of the silicon substrate 100 by using the first photoresist pattern, and removing the first photoresist pattern, and the trenches 101 may be formed to have a predetermined depth during the first etching.

Next, the silicon substrate 100 provided with the trenches 101 is annealed under predetermined temperature, pressure and time conditions, thereby forming the cavity channel 102 in the silicon substrate 100, as shown in FIG. 4.

For reference, referring to FIG. 12, when the silicon substrate 100 provided with the trenches 101 having an approximately circular hole-like shape is annealed, upper end openings of the trenches 101 become slowly narrower and then close, like approximately water drops, and at the same time, lower ends of the trenches 101 become wider. At this time, the lower ends of adjacent trenches 101 are connected to each other, thereby cooperatively forming the cavity channel 102 inside the silicon substrate 101 by the adjacent trenches 101.

In addition, as shown in FIG. 13, the formation degree of the cavity channel 102 may be controlled by properly changing a diameter $\varphi_H$ of the trenches 101, a gap $S_H$ between the trenches 101, and annealing conditions. For example, the formation conditions of the cavity channel 102 such as the height (thickness) of the cavity channel 102, the thickness of an upper closed portion of the cavity channel 102 and the depth of a recess (see reference numeral "201" of FIG. 2) formed on the upper surface of the cavity channel 102 may be changed by controlling the diameter $\varphi_H$ of the trenches 101 and the gap $S_H$ between the trenches 101. Hereinafter, an example in which the annealing is carried out by rapid thermal annealing at a temperature of 1,150° C. and pressure of 1 atm (760 Torr) for a time of 15 minutes will be described. Obviously, the annealing conditions may be properly changed according to requirements.

Next, as shown in FIGS. 5 and 6, after forming the cavity channel 102 inside the silicon substrate 100, a polysilicon thin film layer (Poly-Si LPCVD) 130 may be formed on the upper surface of the silicon substrate 130. For example, the polysilicon thin film layer 130 may be provided by depositing a polysilicon layer 130' on the upper surface of the silicon substrate 130, and polishing the upper surface of the polysilicon layer 130' to remove the upper recess, which may cause problems during a subsequent bonding process.

For reference, the polysilicon thin film layer 130 may be formed for peripheral structures, adhesion or the like. In some cases, another means instead of the polysilicon thin film layer may be used as an alternative means, or the polysilicon thin film layer may be removed.

Next, as shown in FIG. 7, the hollow silicon oxide structure 110 is formed on the inner wall surface of the cavity channel 102 by oxidizing the inner wall surface of the cavity channel 102.

The microstructure is a silicon oxide film formed by oxidizing the inner wall surface of the cavity channel 102 formed inside the silicon substrate 100 and may be formed in a hollow pipe shape corresponding to the cavity channel 102 along the inner wall surface of the cavity channel 102. Unlike the related art, in the present invention, without performing patterning and etching processes in several complicated steps in order to form the hollow silicon oxide structure, simply, the hollow silicon oxide structure may be formed by supplying oxygen along the inner space of the cavity channel 102 and oxidizing the inner wall surface of the cavity channel 102.

For reference, in the embodiment of the present invention, an example in which the polysilicon thin film layer 130 is first formed and the hollow silicon oxide structure 110 is formed is described, but in some cases, the hollow silicon oxide structure may be formed and then the polysilicon thin film layer may be formed.

Next, the periphery of the hollow silicon oxide structure 110 is partially removed such that the hollow silicon oxide structure 110 can resonate with respect to the silicon substrate 100.

For reference, herein, the case where the hollow silicon oxide structure 110 is partially removed such that the hollow silicon oxide structure 110 can resonate with respect to the silicon substrate 100 can be understood as the case where a resonance space 103 is formed by partially removing the silicon substrate 100 portion corresponding to the periphery of the hollow silicon oxide structure 110 so as to have a structure in which the hollow silicon oxide structure 110 can resonate with respect to the silicon substrate 100.

The hollow silicon oxide structure 110 may have various structures, as a structure in which the hollow silicon oxide structure 110 can resonate with respect to the silicon substrate 100, according to requirements and design specifications. For example, by partially removing the periphery of the hollow silicon oxide structure 110, the hollow silicon oxide structure 110 may be provided in a cantilever structure having a fixed end at one end and a free end at the other end. As another example, by partially removing the periphery of the hollow silicon oxide structure 110, the hollow silicon oxide structure 110 may be provided in a bridge structure having fixed ends at both ends.

The process of removing the periphery of the hollow silicon oxide structure 110 may be implemented by various methods according to requirements and design specifications. As an example, the partially removing of the periphery of the hollow silicon oxide structure 110 may include patterning a second photoresist pattern 140 on the upper surface of the silicon substrate 100 as shown in FIG. 8, partially second-etching the periphery of the hollow silicon oxide structure 110 in the silicon substrate 100 by using the second photoresist pattern 140 as shown in FIG. 9, and removing the second photoresist pattern 140.

For reference, a wet or dry etching process using a general photoresist pattern or the like may be applied as the aforementioned first or second etching processes using the first and second photoresist patterns 140, and the present invention is not limited or restricted by a type and characteristics of photoresist pattern and etching process. In addition, the process of removing the first and second photoresist patterns 140 may also be performed by general ashing and stripping processes.

Next, as shown in FIG. 10, a first electrode layer 120 may be formed on an upper surface of the hollow silicon oxide structure 110.

The first electrode layer 120 may be formed by depositing a metal layer on the upper surface of the hollow silicon oxide structure 110. The first electrode layer 120 may be used of various single or alloy metallic materials which can electrostatically interact with a second electrode layer 210 to be described below, and the present invention is not limited or restricted by a type and characteristics of first electrode layer 120. For reference, when power is applied to the second electrode layer 210, the hollow silicon oxide structure 110 can resonate by the first electrode layer 120 that electrostatically interacts with the second electrode layer 210.

Next, as shown in FIG. 11, the glass substrate 200 having the second electrode layer 210 for cooperatively and electrostatically interacting with the first metal layer is adhered to the upper surface of the silicon substrate 100.

The glass substrate 200 may be provided by various methods according to requirements and design specifications. For example, the glass substrate 200 may be provided by patterning a third photoresist pattern on the surface of the glass substrate 200, forming a resonance space on the surface of the glass substrate 200 by third-etching the surface of the glass substrate 200 using the third photoresist pattern, and forming the second electrode layer 210 on the resonance space.

The second electrode layer 210 may be formed of the same or similar material as or to the first electrode layer 120, and external power may be connected to the second electrode layer 210. The glass substrate 200 may be adhered such that the surface formed with the resonance space faces the upper surface (the surface where the hollow silicon oxide structure 110 is exposed) of the silicon substrate 100.

For reference, the hollow silicon oxide structure shown in FIGS. 9 and 11 may be a portion corresponding to an end of a cantilever type of hollow silicon oxide structure.

Furthermore, in the embodiment of the present invention described and illustrated above, an example in which the hollow silicon oxide structure 110 resonates based on electrostatic excitation between the first electrode layer 120 and the second electrode layer 210 is described. However, in some cases, the hollow silicon oxide structure may be configured to resonate by other mechanical excitation methods.

Further, FIG. 14 is a diagram for describing a microchannel resonator according to another embodiment of the present invention.

In the aforementioned embodiment of the present invention, an example in which the hollow silicon oxide structure 110 is provided in the cantilever structure is described, but according to another embodiment of the present invention, the hollow silicon oxide structure 110 may be provided in another structure that can resonate.

Referring to FIG. 14, by partially removing periphery of the hollow silicon oxide structure 110, the hollow silicon oxide structure 110 may be provided in a bridge structure having fixed ends at both ends. For reference, even in the hollow silicon oxide structure 110 in the bridge structure, the hollow silicon oxide structure 110 can also be configured to resonate by the excitation means such as the first electrode layer 120 and the second electrode layer 210.

Hereinafter, preferred embodiments of the present invention will be described in detail with reference to the accompanying drawings, but the present invention is not limited or restricted by the embodiments. For reference, in this specification, the same reference numerals designate substantially the same elements. Under such a rule, contents described in other drawings may be cited and described and contents that are determined obviously to those skilled in the art or repeated may be omitted.

FIGS. 15 and 16 are diagrams for describing a microchannel resonator according to the present invention and FIGS. 17 to 29 are diagrams for describing a method for manufacturing a microchannel resonator according to the present invention.

For reference, the microchannel resonator according to the present invention may be used for measuring the mass and characteristics of objects. In some cases, the microchannel resonator according to the present invention may be used for sensing, measuring, analyzing and diagnosing of physical, chemical and biological interactions of objects to be measured, and the present invention is not limited or restricted to the usage thereof.

Referring to FIGS. 15 and 16, the microchannel resonator according to the present invention includes a silicon substrate 100 and a glass substrate 200.

A microchannel structure is provided on the silicon substrate 100 to resonate, and the microchannel structure can resonate by electrostatic interaction between the first electrode layer 120 formed on the upper surface of the microchannel structure and the second electrode layer 210 provided on the glass substrate 200.

The microchannel structure may be formed in a hollow pipe shape by forming the cavity channel 102 inside the silicon substrate 100, forming the hollow silicon oxide structure 110 on the inner wall surface of the cavity channel by oxidizing the inner wall surface of the cavity channel 102, and then forming a hollow polysilicon structure 112 on the inner wall surface of the hollow silicon oxide structure 110.

For reference, the microchannel structure may be provided in a cantilever structure that has a fixed end at one end and a free end at the other end, but in some cases, the microchannel structure may be provided in a bridge structure having fixed ends at both ends.

Hereinafter, a method for manufacturing a microchannel resonator according to the present invention will be described.

The method for manufacturing the microchannel resonator according to the present invention includes providing a silicon substrate 100, forming a cavity channel 102 inside the silicon substrate 100, forming a hollow silicon oxide structure 110 on the inner wall surface of the cavity channel by oxidizing the inner wall surface of the cavity channel 102, forming a hollow polysilicon structure 112 on the inner wall surface of the hollow silicon oxide structure 110, selectively removing the periphery of the hollow polysilicon structure 112 such that the hollow polysilicon structure 112 can resonate with respect to the silicon substrate 100, and adhering a glass substrate 200 on the upper surface of the silicon substrate 100.

First, the silicon substrate 100 is provided and the cavity channel 102 is formed inside the silicon substrate 100.

The cavity channel 102 inside the silicon substrate 100 may be formed by various methods according to requirements and design specifications. For example, the forming of the cavity channel 102 inside the silicon substrate 100 may include forming a plurality of trenches 101 on the silicon substrate 100, and annealing the silicon substrate 100 using the plurality of trenches 101 so as to form the cavity channel 102 inside the silicon substrate 100, and during annealing of the silicon substrate 100, the adjacent trenches 101 are connected to each other to cooperatively form the cavity channel 102. Referring to FIG. 17, the plurality of trenches 101 may be formed on the silicon substrate 100 at a predetermined array. The trenches 101 may be formed by various methods according to requirements. For example, the forming of the trenches 101 may include patterning a first photoresist pattern on the silicon substrate 100, first-etching the surface of the silicon substrate 100 by using the first photoresist pattern, and removing the first photoresist pattern, and the trenches 101 may be formed to have a predetermined depth during the first etching.

Next, the silicon substrate 100 provided with the trenches 101 is annealed under predetermined temperature, pressure and time conditions to form the cavity channel 102 inside the silicon substrate 100, as shown in FIG. 18. For reference, when the silicon substrate 100 provided with the trenches 101 having an approximately circular hole-like shape is annealed, upper end openings of the trenches 101 become slowly narrower and then closed, like approximately water drops, and at the same time, lower ends of the trenches 101 become wider. At this time, the lower ends of adjacent trenches 101 are connected to each other, thereby cooperatively forming the cavity channel 102 inside the silicon substrate 100 by the adjacent trenches 101 (see FIG. 12).

Furthermore, the formation degree of the cavity channel 102 may be controlled by properly changing a diameter $\varphi_H$ of the trenches 101, a gap $S_H$ between the trenches 101, and annealing conditions (see FIG. 13). For example, the formation conditions of the cavity channel 102 such as the height (thickness) of the cavity channel 102, the thickness of an upper closed portion of the cavity channel 102 and the depth of a recess (see reference numeral "201" of FIG. 16) formed on the upper surface of the cavity channel 102 may be changed by controlling the diameter $\varphi_H$ of the trenches 101 and the gap $S_H$ between the trenches 101. Hereinafter, an example in which the annealing is carried out by rapid thermal annealing at a temperature of 1,150° C. and pressure of 1 atm (760 Torr) for a time of 15 minutes will be described. Obviously, the annealing conditions may be properly changed according to requirements.

Next, as shown in FIGS. 19 and 20, after forming the cavity channel 102 inside the silicon substrate 100, a polysilicon thin film layer (Poly-Si LPCVD) 130 may be formed on the upper surface of the silicon substrate 130. For example, the polysilicon thin film layer 130 may be provided by depositing a polysilicon layer 130' on the upper surface of the silicon substrate 130, and polishing the upper surface of the polysilicon layer 130' to remove the upper recess, which may cause problems during a subsequent bonding process.

For reference, the polysilicon thin film layer 130 may be formed for peripheral structures, adhesion or the like. In some cases, another means instead of the polysilicon thin film layer may be used as an alternative means, or the polysilicon thin film layer may be removed.

Next, as shown in FIG. 21, the hollow silicon oxide structure 110 is formed on the inner wall surface of the cavity channel 102 by oxidizing the inner wall surface of the cavity channel 102.

The hollow silicon oxide structure 110 is a silicon oxide film formed by oxidizing the inner wall surface of the cavity channel 102 formed inside the silicon substrate 100 and may be formed in a hollow pipe shape corresponding to the cavity channel 102 along the inner wall surface of the cavity channel 102. Unlike the related art, in the present invention, without performing patterning and etching processes in several complicated steps in order to form the microchannel structure, simply, the hollow silicon oxide structure may be formed by supplying oxygen along the inner space of the cavity channel 102 and oxidizing the inner wall surface of the cavity channel 102.

For reference, in the embodiment of the present invention, an example in which the polysilicon thin film layer 130 is first formed and the microchannel structure is formed is described, but in some cases, the microchannel structure may be formed and then the polysilicon thin film layer may be formed.

Next, as shown in FIG. 22, a hollow polysilicon structure 112 is formed on the inner wall surface of the hollow silicon oxide structure 110.

The hollow polysilicon structure 112 may be formed by depositing polysilicon on the inner wall surface of the hollow silicon oxide structure 110 and formed in a hollow pipe shape corresponding to the hollow silicon oxide structure 110 along the inner wall surface of the hollow silicon oxide structure 110.

A hollow micro channel structure may be provided such that the moving material resonates by the hollow polysilicon structure 112, and the width and the height of the microchannel structure may be determined by the hollow polysilicon structure 112. The hollow polysilicon structure 112 is formed on the inner wall surface of the hollow silicon oxide structure 110 to have a width and a height which are smaller than those of the hollow silicon oxide structure 110.

Next, the periphery of the hollow polysilicon structure 112 is selectively removed such that the hollow polysilicon structure 112 can resonate with respect to the silicon substrate 100.

In the selectively removing of the periphery of the hollow polysilicon structure 112 in order to form the hollow microchannel structure, the silicon substrate 100 and the hollow silicon oxide structure 110 can be removed by a single removal process or a plurality of removal processes. For example, the silicon substrate 100 and the hollow silicon oxide structure 110 may be simultaneously removed by one etching process, or may be separately removed by a plurality of etching processes.

Hereinafter, an example in which the selectively forming of the periphery of the hollow polysilicon structure 112 in order to form the hollow microchannel structure includes selectively removing the silicon substrate 100 corresponding to the periphery of the hollow silicon oxide structure 110 and removing the hollow silicon oxide structure 110 exposed by selectively removing the silicon substrate 100 will be described.

For reference, the case where the hollow polysilicon structure 112 is selectively removed such that the hollow polysilicon structure 112 can resonate with respect to the silicon substrate 100 can be understood as the case where a resonance space 103 is formed by removing the silicon substrate 100 portion corresponding to the periphery of the hollow polysilicon structure 112 and the hollow silicon oxide structure 110 so as to have a structure in which the hollow polysilicon structure 112 can resonate with respect to the silicon substrate 100.

As a structure in which the microchannel structure configured by the hollow polysilicon structure 112 can resonate with respect to the silicon substrate 100, various structures may be applied according to requirements and design specifications. For example, by selectively removing the periphery of the hollow polysilicon structure 112, the microchannel structure configured by the hollow polysilicon structure 112 may be provided in a cantilever structure having a fixed end at one end and a free end at the other end. As another example, by selectively removing the periphery of the hollow polysilicon structure 112, the microchannel structure configured by the hollow polysilicon structure 112 may be provided in a bridge structure having fixed ends at both ends.

The process of removing the silicon substrate 100 portion corresponding to the periphery of the hollow polysilicon structure 112 may be implemented by various methods according to requirements and design specifications. As an example, the removing of the silicon substrate 100 portion corresponding to the periphery of the hollow polysilicon structure 112 may include patterning a second photoresist pattern 140 on the upper surface of the silicon substrate 100 as shown in FIG. 23, partially second-etching the periphery of the hollow polysilicon structure 112 in the silicon substrate 100 by using the second photoresist pattern 140 as shown in FIG. 24, and removing the second photoresist pattern 140 as shown in FIG. 25.

For reference, a wet or dry etching process using a general photoresist pattern or the like may be applied as the aforementioned first or second etching processes using the first and second photoresist patterns 140, and the present invention is not limited or restricted by a type and characteristics of photoresist pattern and etching process. In addition, the process of removing the first and second photoresist patterns 140 may also be performed by general ashing and stripping processes.

Referring to FIG. 26, as described above, by removing the silicon substrate 100 portion corresponding to the periphery of the hollow polysilicon structure 112 and the hollow silicon oxide structure 110, the microchannel structure configured by the remaining hollow polysilicon structure 112 may be provided in a structure which can resonate with respect to the silicon substrate 100.

Meanwhile, according to the present invention, processes of forming and removing a second hollow silicon oxide structure 110a and a second hollow polysilicon structure 112a inside the microchannel structure configured by the hollow polysilicon structure 112 are repetitively performed to reduce the height and the width of the microchannel structure.

Referring to FIG. 27, the method for manufacturing the microchannel resonator according to the present invention may further include forming the second hollow silicon oxide structure 110a on the inner wall surface of the hollow polysilicon structure 112 by oxidizing the inner wall surface of the hollow polysilicon structure 112, forming the second hollow polysilicon structure 112a inside the second hollow silicon oxide structure 110a, and removing the second hollow silicon oxide structure 110a. Heights H1 and H2 and widths W1 and W2 of the microchannel structure may be reduced by using the second hollow silicon oxide structure 110a and the second hollow polysilicon structure 112a.

For reference, the case where the heights and the widths of the microchannel structure are reduced by using the second hollow silicon oxide structure 110a and the second hollow polysilicon structure 112a can be understood as the case where a microchannel structure having relatively smaller height and width than the microchannel structure configured by the aforementioned hollow polysilicon structure 112 is formed.

Furthermore, in FIG. 27, an example in which the second hollow silicon oxide structure 110a and the second hollow polysilicon structure 112a are formed once is described. However, in some cases, a microchannel structure having finer height and width may be formed by repetitively forming and removing another second hollow silicon oxide structure and another second hollow polysilicon structure inside the microchannel structure configured by the second hollow polysilicon structure.

As such, according to the present invention, the processes of forming and removing the second hollow silicon oxide structure 110a and the second hollow polysilicon structure 112a are repetitively performed to form a channel structure having very small width and height, and a channel resonator of a nano-scale unit as well as a micro-scale unit can be manufactured.

Meanwhile, the channel resonator of the nano-scale unit can be formed by forming trenches for forming the cavity channel with a very fine size (a nano scale), but in order to form the trenches with the very fine size, there is a problem in that complicated manufacturing processes need to be performed by using expensive specific equipment. However, according to the present invention, without forming the trenches having the very fine sizes, simply, the processes of forming and removing the second hollow silicon oxide structure 110a and the second hollow polysilicon structure 112a are repetitively performed to manufacture a channel resonator of a nano-scale unit.

In the embodiment of the present invention described and illustrated above, an example in which the second hollow silicon oxide structure and the second hollow polysilicon structure are formed inside the remaining hollow polysilicon structure after removing the silicon substrate and the hollow silicon oxide structure 110 is described. However, in some cases, before removing the silicon substrate and the hollow silicon oxide structure, the second hollow silicon oxide structure and the second hollow polysilicon structure can be formed inside the hollow polysilicon structure.

Next, as shown in FIG. 28, a first electrode layer 120 may be formed on an upper surface of the microchannel structure configured by the hollow polysilicon structure 112 (alternatively, the second hollow polysilicon structure).

The first electrode layer 120 may be formed by depositing a metal layer on the upper surface of the microchannel structure. The first electrode layer 120 may be used of various single or alloy metallic materials which can electrostatically interact with a second electrode layer 210 to be described below, and the present invention is not limited or restricted by a type and characteristics of first electrode layer 120. For reference, when power is applied to the second electrode layer 210, the microchannel structure can resonate by the first electrode layer 120 that electrostatically interacts with the second electrode layer 210.

Next, as shown in FIG. 29, the glass substrate 200 having the second electrode layer 210 for cooperatively and electrostatically interacting with the first metal layer is adhered to the upper surface of the silicon substrate 100.

The glass substrate 200 may be provided by various methods according to requirements and design specifications. For example, the glass substrate 200 may be provided by patterning a third photoresist pattern (not shown) on the surface of the glass substrate 200, third-etching the surface of the glass substrate 200 using the third photoresist pattern to form a resonance space on the surface of the glass substrate 200, and forming a second electrode layer 210 on the resonance space.

The second electrode layer 210 may be formed of the same or similar material as or to the first electrode layer 120, and external power may be connected to the second electrode layer 210. The glass substrate 200 may be adhered such that the surface formed with the resonance space faces the upper surface (the surface where the microchannel structure 110 is exposed) of the silicon substrate 100.

For reference, the microchannel structure 102 shown in FIGS. 28 and 29 may be a portion corresponding to an end of a cantilever type of microchannel structure.

Furthermore, in the embodiment of the present invention described and illustrated above, an example in which the microchannel structure resonates based on electrostatic excitation between the first electrode layer 120 and the second electrode layer 210 is described. However, in some cases, the microchannel structure may be configured to resonate by other mechanical excitation methods.

In the aforementioned embodiment of the present invention, an example in which the microchannel structure is provided in the cantilever structure is described, but according to another embodiment of the present invention, the microchannel structure may be provided in another structure that can resonate.

By selectively removing the periphery of the microchannel structure, the microchannel structure may be provided in a bridge structure having fixed ends at both ends (see FIG. 14). For reference, even in the microchannel structure in the bridge structure, the microchannel structure can also be configured to resonate by the excitation means such as the first electrode layer and the second electrode layer.

Although the present invention has been disclosed with reference to the preferred embodiments, those skilled in the art will appreciate that various modifications, additions and substitutions are possible, without departing from the scope and spirit of the invention as disclosed in the accompanying claims.

The invention claimed is:

1. A method for manufacturing a microchannel resonator capable of measuring a mass and characteristics of an object using a principle in which a resonance frequency is changed according to a mass of a moving material, the method comprising:
    providing a silicon substrate;
    forming a cavity channel inside the silicon substrate;
    forming a hollow silicon oxide structure on the inner wall surface of the cavity channel by oxidizing the inner wall surface of the cavity channel;
    forming a hollow polysilicon structure on the inner wall surface of the hollow silicon oxide structure; and
    selectively removing the periphery of the hollow polysilicon structure such that the hollow polysilicon structure resonates with respect to the silicon substrate,
    wherein a hollow microchannel structure is provided such that the moving material resonates by the remaining hollow polysilicon structure by selectively removing the periphery of the hollow polysilicon structure.

2. The method for manufacturing a microchannel resonator according to claim 1, wherein the forming of the cavity channel inside the silicon substrate includes
    forming a plurality of trenches on the silicon substrate; and
    annealing the silicon substrate to form the cavity channel inside the silicon substrate by using the plurality of trenches,
    wherein during the annealing of the silicon substrate, the adjacent trenches are connected to each other and cooperatively form the cavity channel.

3. The method for manufacturing a microchannel resonator according to claim 2, wherein the forming of the trenches includes
    patterning a first photoresist pattern on the silicon substrate;
    first-etching the surface of the silicon substrate by using the first photoresist pattern; and
    removing the first photoresist pattern,
    wherein the trenches are formed during the first etching.

4. The method for manufacturing a microchannel resonator according to claim 1, wherein the partially removing of the periphery of the hollow silicon oxide structure includes
    patterning a second photoresist pattern of the silicon substrate;
    partially second-etching the periphery of the hollow silicon oxide structure on the silicon substrate by using the second photoresist pattern; and
    removing the second photoresist pattern.

5. The method for manufacturing a microchannel resonator according to claim 1, wherein by partially removing the periphery of the hollow silicon oxide structure, the hollow silicon oxide structure is provided in a cantilever structure having a fixed end at one end and a free end at the other end.

6. The method for manufacturing a microchannel resonator according to claim 1, wherein by partially removing the periphery of the hollow silicon oxide structure, the hollow silicon oxide structure is provided in a bridge structure having fixed ends at both ends.

7. The method for manufacturing a microchannel resonator according to claim 1, further comprising:
    forming a polysilicon thin film layer on an upper surface of the silicon substrate after forming the cavity channel.

8. The method for manufacturing a microchannel resonator according to claim 7, wherein the forming of the polysilicon thin film layer includes
    depositing a polysilicon layer on the upper surface of the silicon substrate; and
    polishing the upper surface of the silicon substrate such that an upper recess of the polysilicon layer is removed.

9. The method for manufacturing a microchannel resonator according to claim 1, further comprising:
    adhering a glass substrate to the silicon substrate.

10. The method for manufacturing a microchannel resonator according to claim 9, further comprising:
    forming a first electrode layer on the upper surface of the hollow silicon oxide structure before adhering the glass substrate,
    wherein a second electrode layer for cooperatively and electrostatically interacting with the first electrode layer is provided on the glass substrate.

11. The method for manufacturing a microchannel resonator according to claim 10, wherein the glass substrate is provided by a process including patterning a third photoresist pattern on the surface of the glass substrate; forming a resonance space on the surface of the glass substrate by third-etching the surface of the glass substrate by using the third photoresist pattern; and forming the second electrode layer on the resonance space.

12. The method for manufacturing a microchannel resonator according to claim 1, wherein in the selectively removing of the periphery of the hollow polysilicon structure such that the hollow polysilicon structure resonates with respect to the silicon substrate, the silicon substrate and the hollow polysilicon structure are removed by a single removing process or a plurality of removing processes.

13. The method for manufacturing a microchannel resonator according to claim 1, further comprising:
    forming a second hollow silicon oxide structure on the inner wall surface of the hollow polysilicon structure by oxidizing the inner wall surface of the hollow polysilicon structure;
    forming a second hollow polysilicon structure inside the second hollow silicon oxide structure; and
    removing the second hollow silicon oxide structure,
    wherein the microchannel structure is defined by the second hollow polysilicon structure and a height and a width of the microchannel structure are reduced by using the second hollow silicon oxide structure and the second hollow polysilicon structure.

14. The method for manufacturing a microchannel resonator according to claim 1, wherein by selectively removing the periphery of the second hollow polysilicon structure, the microchannel structure is provided in a cantilever structure having a fixed end at one end and a free end at the other end or in a bridge structure having fixed ends at both ends.

* * * * *